United States Patent [19]

Takeshiba et al.

[11] Patent Number: 4,661,486
[45] Date of Patent: Apr. 28, 1987

[54] PYRIDAZINONE DERIVATIVES AND THEIR USE AS AGRICULTURAL FUNGICIDES

[75] Inventors: Hideo Takeshiba; Takao Kinoto; Teruomi Jojima, all of Hiromachi, Japan

[73] Assignee: Sankyo Company Limited, Tokyo, Japan

[21] Appl. No.: 649,499

[22] Filed: Sep. 11, 1984

[30] Foreign Application Priority Data

Sep. 16, 1983 [JP] Japan .................... 58-170793

[51] Int. Cl.⁴ .................... C07D 237/04; A01N 43/58
[52] U.S. Cl. .................... 514/252; 544/240
[58] Field of Search ................ 544/239, 240; 514/252

[56] References Cited

U.S. PATENT DOCUMENTS

| 3,825,540 | 7/1984 | Laborit | 544/239 |
| 4,052,395 | 10/1977 | Jojima | 544/239 |
| 4,360,672 | 11/1982 | Parg | 544/240 |
| 4,397,854 | 8/1983 | Sircar | 544/239 |
| 4,411,691 | 10/1983 | Rohr | 544/239 |

FOREIGN PATENT DOCUMENTS

| 85985 | 8/1983 | European Pat. Off. | 544/239 |
| 59-139364 | 8/1984 | Japan | 544/240 |

OTHER PUBLICATIONS

Mitsubishi, Chem. Abs. 98, 173193s (1-18-83).
Raninger, Chem. Abs. 92, 58801c (1979).
Konecny et al, Chem. Abs. 94, 84044a (1981).
Teruomi et al, Chem. Abs. 99, 70745q (2-16-83).

Primary Examiner—Mark L. Berch
Attorney, Agent, or Firm—Frishauf, Holtz, Goodman & Woodward

[57] ABSTRACT

Compounds of formula (I):

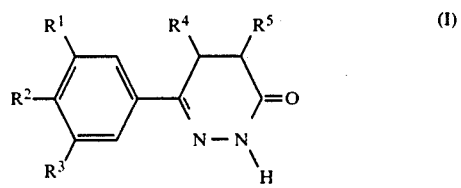

(in which $R^1$ and $R^3$ are hydrogen or halogen; $R^2$ is hydrogen, alkyl, alkoxy or halogen; $R^4$ is hydrogen and $R^5$ is hydroxy or alkoxy; or $R^4$ is hydroxy and $R^5$ is hydrogen; except that $R^1$, $R^2$ and $R^3$ may not all simultaneously be hydrogen) are valuable agricultural fungicides.

19 Claims, No Drawings

PYRIDAZINONE DERIVATIVES AND THEIR USE AS AGRICULTURAL FUNGICIDES

BACKGROUND TO THE INVENTION

The present invention relates to a series of new 6-(substituted phenyl)-4,5-dihydro-2H-pyridazin-3-one derivatives and to their use as agricultural fungicides.

A number of pyridazinone derivatives is known to have fungicidal activity. For example, those derivatives disclosed in United Kingdom Patent Specification No. 1,533,010, of which the most relevant may be represented by the formula:

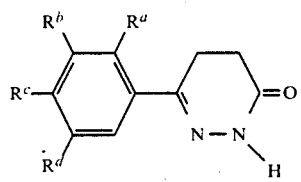

(in which $R^a$ may represent a hydrogen atom, a hydroxy group or an acyloxy group, $R^b$ and $R^d$ both represent halogen atoms or one represents a halogen atom and the other represents a hydrogen atom, and $R^c$ represents, inter alia, a hydrogen or halogen atom or an alkyl or alkoxy group) have been found to be effective against a wide range of pathogenic fungi whilst not exhibiting any phytotoxicity, when employed at effective doses.

Rather similar compounds, but having a substituent at the 2-nitrogen atom of the pyridazinone system are disclosed in European Patent Publication No. 72238, again having good fungicidal activity.

Moreover, closer prior art, in that it has a substituent at the 4-position of the pyridazinone system, is 4-hydroxy-6-phenyl-4,5-dihydro-2H-pyridazin-3-one, which is disclosed in Japanese Patent Application Kokai No. 145685/79 as an intermediate in the preparation of various herbicidal compounds. Japanese Patent Application Kokai No. 8016/83 discloses various 6-(substituted phenyl)-4,5-dihydro-2H-pyridazin-3-one derivatives which may have a variety of substituents, including alkoxy groups, on the pyridazinone system; the substituents on the phenyl moiety, however, differ substantially from those in the present invention and the only specific compound having an alkoxy group (specifically an ethoxy group) on the pyridazinone system differs from the compounds of the present invention in that the substituted phenyl group of the 6-position is replaced by a tetrahydroquinazoline system. The activity described for these latter compounds is said to be a cardiac activity. No fungicidal activity is disclosed for any of the compounds of Japanese Patent Applications Kokai No. 145685/79 and No. 8016/83.

BRIEF SUMMARY OF INVENTION

We have now discovered a series of novel pyridazinone derivatives having excellent fungicidal activities, notably but not exclusively when applied to the water of paddy fields, and which are not phytotoxic at effective doses.

The compounds of the invention may be represented by the formula (I):

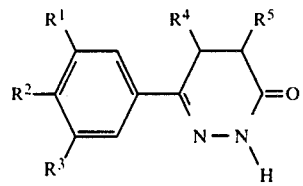

(in which:
$R^1$ and $R^3$ are the same or different and each represents a hydrogen or halogen atom;
$R^2$ represents hydrogen, a $C_1$-$C_3$ alkyl group, a $C_1$-$C_3$ alkoxy group or a halogen atom, provided that at least one of $R^1$, $R^2$ and $R^3$ represents a group or atom other than hydrogen;
and either
$R^4$ represents hydrogen and $R^5$ represents hydroxy or a $C_1$-$C_3$ alkoxy group;
or
$R^4$ represents hydroxy and $R^5$ represents hydrogen.

The compounds of the invention may be prepared by reacting a compound of formula (II):

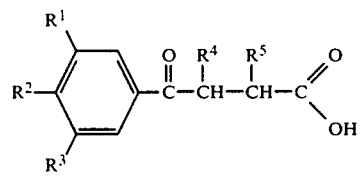

(in which $R^1$, $R^2$, $R^3$, $R^4$ and $R^5$ are as defined above) with hydrazine.

The invention also provides an agricultural fungicidal composition comprising a fungicide in admixture with an agriculturally acceptable carrier or diluent, wherein the fungicide is at least one compound of formula (I).

The invention still further provides a method of preventing or controlling fungal attack on plant material (including seeds and growing plants) by applying to said material or to a locus including the same an effective amount of a fungicide, wherein the fungicide comprises at least one compound of formula (I).

DETAILED DESCRIPTION OF INVENTION

In the compounds of the invention, where $R^1$, $R^2$ or $R^3$ represents a halogen atom, this may be a chlorine, bromine, fluorine or iodine atom, preferably bromine or chlorine.

Where $R^2$ represents a $C_1$-$C_3$ alkyl group, this may be a straight or branched chain group having from 1 to 3 carbon atoms, specifically the methyl, ethyl, propyl and isopropyl groups; of these, the methyl and ethyl, especially the methyl, groups are preferred.

Where $R^2$ or $R^5$ represents an alkoxy group, this likewise may be a straight or branched chain group having from 1 to 3 carbon atoms, specifically the methoxy, ethoxy, propoxy and isopropoxy groups, of which the methoxy, ethoxy and propoxy, especially the methoxy, groups are preferred.

A preferred class of compound of the present invention comprises:
(A) compounds in which:
$R^1$ represents a halogen atom;
$R^2$ represents hydrogen, a halogen atom or a $C_1$-$C_3$ alkyl group; and $R^3$ represents a hydrogen or halogen atom, more preferably:

(B) compound in which:
$R^1$ and $R^3$ both represent halogen atoms (which may be the same or different); and
$R^2$ represents a $C_1$-$C_3$ alkyl group or a halogen atom or (C) compounds in which:
$R^1$ represents a halogen atom;
$R^2$ represents a hydrogen or halogen atom; and
$R^3$ represents hydrogen.

In particular, we prefer:

(D) compounds as defined in (A), (B) and (C) above, in which $R^4$ represents hydroxy and $R^5$ represents hydrogen or (E) compounds as defined in (A), (B) and (C) above, in which $R^4$ represents hydrogen and $R^5$ represents methoxy.

Preferred examples of compounds of the present invention are given in the following list; hereafter, where appropriate, the numbers appended to the compounds in this list are used to identify the compounds:

1. 6-(3-bromophenyl)-5-hydroxy-4,5-dihydro-2H-pyridazin-3-one
2. 5-hydroxy-6-(3-iodophenyl)-4,5-dihydro-2H-pyridazin-3-one
3. 5-hydroxy-6-(4-methylphenyl)-4,5-dihydro-2H-pyridazin-3-one
4. 6-(4-ethoxyphenyl)-5-hydroxy-4,5-dihydro-2H-pyridazin-3-one
5. 6-(3,4-dichlorophenyl)-5-hydroxy-4,5-dihydro-2H-pyridazin-3-one
6. 6-(3-chloro-4-isopropylphenyl)-5-hydroxy-4,5-dihydro-2H-pyridazin-3-one
7. 6-(3,5-dichloro-4-methylphenyl)-5-hydroxy-4,5-dihydro-2H-pyridazin-3-one
8. 6-(3,5-dichloro-4-ethylphenyl)-5-hydroxy-4,5-dihydro-2H-pyridazin-3-one
9. 6-(3,5-dichloro-4-methoxyphenyl)-5-hydroxy-4,5-dihydro-2H-pyridazin-3-one
10. 6-(3-bromophenyl)-4-hydroxy-4,5-dihydro-2H-pyridazin-3-one
11. 6-(4-chlorophenyl)-4-hydroxy-4,5-dihydro-2H-pyridazin-3-one
12. 6-(4-fluorophenyl)-4-hydroxy-4,5-dihydro-2H-pyridazin-3-one
13. 4-hydroxy-6-(4-methylphenyl)-4,5-dihydro-2H-pyridazin-3-one
14. 4-hydroxy-6-(4-methoxyphenyl)-4,5-dihydro-2H-pyridazin-3-one
15. 6-(3,4-dichlorophenyl)-4-hydroxy-4,5-dihydro-2H-pyridazin-3-one
16. 6-(3,5-dichloro-4-methylphenyl)-4-hydroxy-4,5-dihydro-2H-pyridazin-3-one
17. 6-(3-bromophenyl)-4-methoxy-4,5-dihydro-2H-pyridazin-3-one
18. 4-methoxy-6-(4-methylphenyl)-4,5-dihydro-2H-pyridazin-3-one
19. 6-(3,4-dichlorophenyl)-4-methoxy-4,5-dihydro-2H-pyridazin-3-one
20. 6-(3,5-dichloro-4-methylphenyl)-4-methoxy-4,5-dihydro-2H-pyridazin-3-one Of the compounds listed above, preferred compounds are Compounds No. 1, 5, 7, 10, 15, 16, 17, 19 and 20, more preferred compounds being Compounds No. 1, 5, 7 and 17.

The compounds of the invention may be prepared by reacting the aforementioned compound of formula (II) with hydrazine. Details of the preparation of these compounds of formula (II) and the reaction thereof with hydrazine are given in the following Methods A, B and C.

METHOD A

Compounds of formula (IA), that is compounds of formula (I) in which $R^4$ represents hydroxy and $R^5$ represents hydrogen, can be prepared as illustrated in the following reaction scheme:

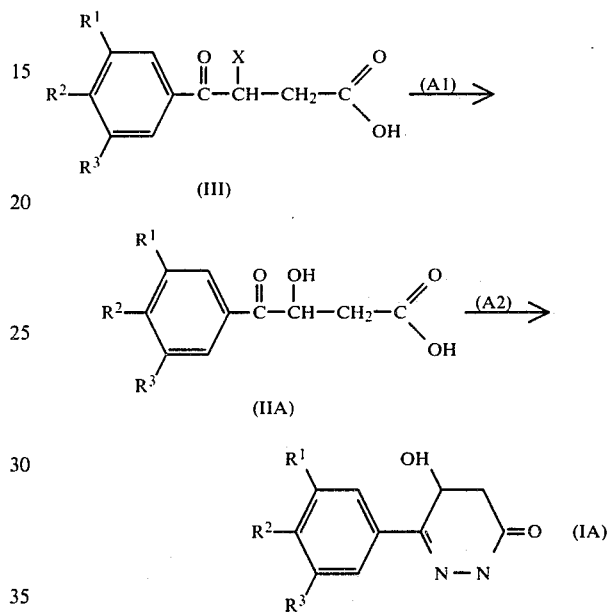

(in which $R^1$, $R^2$ and $R^3$ are as defined above and X represents a halogen atom, preferably chlorine).

Step (A1) consists of reacting the 3-halo-4-(substituted phenyl)-4-oxobutyric acid (III) with a base to give the corresponding 3-hydroxy-4-(substituted phenyl)-4-oxobutyric acid (IIA). This may be carried out according to the procedure described in J. Pharm. Science, 66, 466 (1977).

In step (A2), the resulting 3-hydroxy-4-(substituted phenyl)-4-oxobutyric acid (IIA) is reacted with hydrazine to give the desired product of formula (IA) The hydrazine is preferably employed in the form of its hydrate or of a salt with a mineral acid, such as hydrochloric acid or sulfuric acid. We prefer to employ equimolar amounts of hydrazine and said acid (IIA) or an excess of hydrazine.

The reaction is preferably effected in the presence of an inert solvent, the nature of which is not critical, provided that it has no adverse effect upon the reaction. Suitable solvents include: alcohols, such as methanol, ethanol and isopropanol; organic acids, such as acetic acid; and water; of these, alcohols are preferred.

We normally prefer to carry out the reaction at a temperature ranging from ambient temperature to the reflux temperature of the reaction medium, most preferably at about ambient temperature, as the compounds of formula (I) are rather unstable and may, at elevated temperatures, eliminate the hydroxy or alkoxy group represented by $R^4$ or $R^5$, with formation of a double bond.

METHOD B

Compounds of formula (IB), that is to say compounds of formula (I) in which $R^5$ represents a $C_1$-$C_3$ alkoxy group, may be prepared as illustrated in the following reaction scheme:

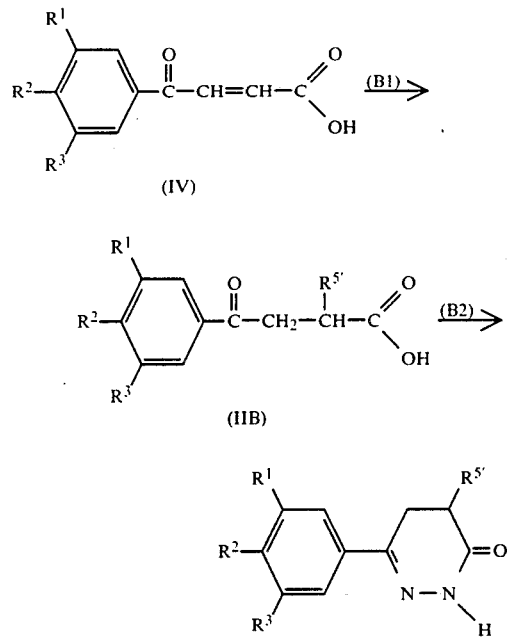

In the above formulae, $R^1$, $R^2$ and $R^3$ are as defined above and Rhu 5' represents a $C_1$-$C_3$ alkoxy group.

In step (B1), the 4-(substituted phenyl)-4-oxo-2-butenoic acid of formula (IV) is reacted with a $C_1$-$C_3$ alkanol in the presence of a base to give the corresponding 2-alkoxy-4-(substituted phenyl)-4-oxobutyric acid of formula (IIB); this reaction may be carried out following the procedure described in Japanese Patent Application Kokoku No. 56-428.

Step (B2) of this Method comprises reacting this acid (IIB) with hydrazine, which may be in the form of its hydrate or a salt, and is carried out under the same conditions as are employed in step (A2) of Method A.

METHOD C

Compounds of formula (IC), that is to say compounds of formula (I) in which $R^5$ represents a hydroxy group, may be prepared by the process illustrated in the following reaction scheme:

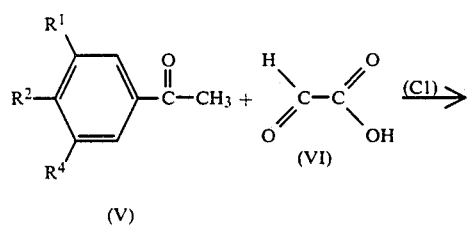

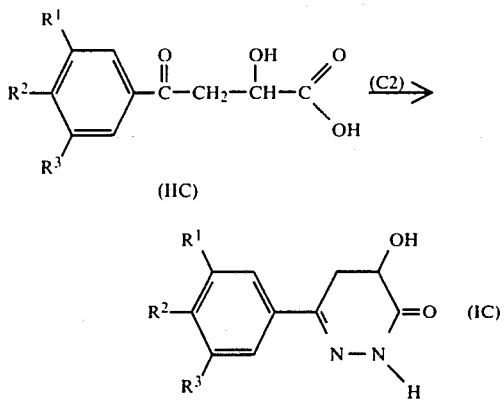

In the above formulae, $R^1$, $R^2$ and $R^3$ are as defined above.

In step (C1) of this Method, an acetophenone of formula (V) is reacted with glyoxylic acid (VI), preferably in the form of its hydrate, to give the 2-hydroxy-4-(substituted phenyl)-4-oxobutyric acid of formula (IIC), following the procedure described in West German Offenlegungsschrift No. 1,695,694.

This acid (IIC) is then reacted with hydrazine in step (C2), following the procedure described in step (A2) of Method A.

The compounds of the invention, prepared by any of the above Methods, may then be separated from the reaction mixture and, if desired, further purified, by conventional means.

The compounds of the invention may be employed as agricultural fungicides and show a preventive and curative effect against plant diseases, without damaging the host plants.

Specifically, they are particularly effective in the control of sheath blight, which is a very serious disease attacking rice plants; for this purpose, they are preferably employed in the form of a spray, particularly a foliar spray, or are applied, dissolved or dispersed in water, to the soil surface.

They also effectively control damping-off of various crops, such as beet, cotton plants and plants of the gourd family, which disease is caused by pathogenic fungi of the class Rhizoctonia. They are also effective in the control of infectious soil-borne diseases, for example southern blight (which attacks the egg-plant and plants of the gourd family) and black scurf (which attacks potatoes); in this case, they are preferably employed in the form of a soil fungicide or a seed disinfectant.

At effective doses, the compounds of the invention do not exhibit any phytotoxicity to such plants as rice plants, tomato plants, potatoes, cotton plants, egg-plants, cucumbers and kidney beans. Moreover, they may be used effectively as fungicides in orchards, non-crop land and forests.

The compounds of the invention may be formulated as preparations of the type commonly employed as agricultural fungicides, for example powdery dusts, coarse dusts, fine granules, coarse granules, wettable powders, emulsifiable concentrates, aqueous liquids, water-soluble powders and oil suspensions, by mixing them with a carrier and, if required, with other auxiliary agents. The carrier employed may be natural or synthetic and organic or inorganic; it is mixed with the active compound to assist that compound to reach the material to be treated and to make it easier to store, transport or handle the active compound.

Suitable solid carriers are: inorganic substances, such as clays (examples of which are kaolinite, montmorillonite or attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; vegetable organic substances, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes, such as carnauba wax and beeswax; and urea.

Examples of suitable liquid carriers are: paraffinic or naphthenic hydrocarbons, such as kerosine, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, monochlorobenzene and o-chlorotoluene; ethers, such as dioxane and tetrahydrofuran; ketones such as acetone, methyl ethyl ketone, diisobutyl ketone, cyclohexanone, acetophenone and isophorone; esters, such as ethyl acetate, amyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol monoethyl ether, ethylene glycol monophenyl ether, diethylene glycol monoethyl ether and diethylene glycol monobutyl ether; polar solvents, such as dimethylformamide and dimethyl sulphoxide; and water.

The fungicidal compositions of the present invention may contain surface active agents to emulsify, disperse, wet, spread, bind, control disintegration of, improve fluidity of or rust-proof the fungicidal composition or to stabilize the active compound; although any of the conventional classes of surface active agent, be they nonionic, anionic, cationic or amphoteric, may be employed, we prefer to employ non-ionic and/or anionic surface active agents. Examples of suitable non-ionic surface active agents are: the polymerization adducts of ethylene oxide with higher alcohols, such as lauryl alcohol, stearyl alcohol or oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di-alkylphosphoric acids, such as stearylphosphoric acid or dilaurylphosphoric acid; the polymerization adducts of ethylene oxide with amines, such as dodecylamine; the polymerization adducts of ethylene oxide with higher fatty acid amides, such as stearamide; the polymerization adducts of ethylene oxide with higher fatty acid esters of polyhydric alcohols, such as sorbitan, and said fatty acid esters themselves; and the polymerization adducts of ethylene oxide with propylene oxide.

Examples of suitable anionic surface active agents are: alkyl sulfate salts, such as sodium lauryl sulfate or oleyl sulfate amine salt; alkyl sulfonate salts, such as sodium dioctyl sulfosuccinate or sodium 2-ethylhexene sulfonate; and aryl sulfonate salts, such as sodium isopropylnaphthalane sulfonate, sodium methylenebisnaphthalene sulfonate, sodium ligninsulfonate or sodium dodecylbenzene sulfonate.

Moreover, the agricultural fungicidal compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the composition of the invention.

The above-mentioned carriers and various auxiliary agents may be used alone or in any desired combination, depending upon the type of preparation, the application and other factors.

In general, the fungicial composition of the present invention may contain the compound of the invention in an amount of from 0.1 to 99% by weight, based upon the weight of the composition, although the precise amount of active ingredient in the composition will, naturally, depend upon the form of the composition, the manner in which it is to be applied and on whether or not the composition contains any other active ingredient.

For example, dusts may conveniently contain from 1 to 25% by weight of the compound of formula (I), the remainder being a solid carrier.

Wettable powders may conveniently contain, for example, from 25 to 90% by weight of the compound (I), the remainder being a solid carrier and a dispersing and wetting agent, if required, together with a protective colloidal agent, a thixotropic agent and an anti-foaming agent.

Granules may conveniently contain from 1 to 35% by weight of the compound of formula (I), a major portion of the remainder being a solid carrier. The active compound is homogeneously admixed with the solid carrier or is adhered to or adsorbed onto the carrier surface; the diameter of each granule is preferably from 0.2 to 1.5 mm.

Emulsifiable concentrates may conveniently contain, for example, from 5 to 50% by weight of the compound of formula (I) and from 5 to 20% by weight of an emulsifying agent, the remainder being a liquid carrier, together with, if required, a corrosion inhibitor.

The fungicidal compositions of the present invention, which are formulated into the various types of preparation described above, may be applied to a paddy or upland (dry) field in an amount of from 1 to 5000 g, more preferably from 10 to 1000 g, of the compound of formula (I) per 10 ares for pre- or post-emergence fungicidal activity; they may be applied by foliage spraying, soil drenching, spraying onto irrigation water or any other known method.

The fungicidal composition of the present invention, when employed for seed disinfection or coating, may effectively control soil-borne or seed infectious diseases by coating seeds in an amount of from 0.01 to 2%, preferably from 0.2 to 0.5%, by weight of the compound of formula (I), based on the weight of the seed.

The fungicidal composition of the present invention may additionally contain other fungicides in order to broaden the fungicidal spectrum and, in some cases, a synergistic effect may be observed. The composition may also contain plant growth regulators, herbicides, insecticides or fertilizers, as is well known in the art.

The fungicidal compositions of the present invention may also be used together with control agents effective against rice blast, helminthosporium leaf spot, bacterial leaf blight, rice stem borers, planthoppers and/or leafhoppers, to save the labor involved in separate applications. A combination of one or more of these additional control agents with the composition of the invention may be employed, depending upon the disease and/or the insect to be controlled and the form of the composition to be employed.

The invention is further illustrated by the following Examples, of which Examples 1 to 3 illustrate the preparation of compounds of the invention, Examples 4 to 6 illustrate the preparation of compositions of the invention and Examples 7 to 9 illustrate the biological activity of the compounds. The Preparations illustrate the preparation of starting materials used in Examples 1 to 3. In all of these Examples, all parts are by weight.

EXAMPLE 1

6-(3,5-Dichloro-4-methylphenyl)-5-hydroxy-4,5-dihydro-2H-pyridazin-3-one (Compound No. 7)

A mixture of 2.77 g of 4-(3,5-dichloro-4-methylphenyl)-3-hydroxy-4-oxobutyric acid (prepared as described in Preparation 1), 0.5 g of hydrazine hydrate (100%) and 20 ml of ethanol was stirred at room temperature for 6 hours. The resulting white powder was then collected by filtration, to give 1.77 g (yield 65%) of the desired Compound No. 7, melting at 253°–256° C.

Infrared Absorption Spectrum (Nujol-trademark mull) $\nu_{max}$ cm$^{-1}$: 3460, 3240, 3100, 2800–2200, 1690.

Nuclear Magnetic Resonance Spectrum (hexadeuterated dimethyl sulfoxide) δ ppm: 11.11 (1H, singlet, NH); 7.70 (2H, singlet, aromatic hydrogens); 5.77 (1H, broad singlet, OH); 4.75 (1H, triplet, J=6 Hz, hydrogen at 5-position of pyridazine); 2.5–3.0 (2H, multiplet, hydrogens at 4-position of pyridazine); 2.43 (3H, singlet, CH$_3$).

Following the same procedure, the following compounds were also prepared:
6-(3-bromophenyl)-5-hydroxy-4,5-dihydro-2H-pyridazin-3-one (Compound No. 1), melting at 148°–151° C.;
6-(3,4-dichlorophenyl)-5-hydroxy-4,5-dihydro-2H-pyridazin-3-one (Compound No. 5), melting at 210°–220° C.;
6-(3,5-dichloro-4-methoxyphenyl)-5-hydroxy-4,5-dihydro-2H-pyridazin-3-one (Compound No. 9), melting at 175°–178° C.; and
5-hydroxy-6-(4-methylphenyl)-4,5-dihydro-2H-pyridazin-3-one (Compound No. 3), melting at 179°–181° C.

EXAMPLE 2

4-Methoxy-6-(4-methylphenyl)-4,5-dihydro-2H-pyridazin-3-one (Compound No. 18)

0.5 g of hydrazine hydrate (100%) was added, at room temperature, to a solution of 2.22 g of 2-methoxy-4-(4-methylphenyl)-4-oxobutyric acid (prepared as described in Preparation 2) in 20 ml of methanol, and the mixture was allowed to stand at room temperature overnight. The crystals which precipitated were collected by filtration and washed with methanol, to give 1.35 g of the title compound. The filtrate was concentrated by evaporation at 50° C. and the resulting residue was washed with methanol, giving a further 0.5 g of the pure title compound, melting at 167°–169.5° C. The total yield was 85%.

Infrared Absorption Spectrum (Nujol mull) $\nu_{max}$ cm$^{-1}$: 3200, 3100, 2800–2100, 1660, 1600.

Nuclear Magnetic Resonance Spectrum (CDCl$_3$) δ ppm: 9.42 (1H, singlet, NH); 7.23, 7.68 (4H, AB doublet, J=8 Hz, aromatic hydrogens); 3.93 (1H, triplet, J=6 Hz, hydrogen at 4-position of pyridazine); 3.57 (3H, singlet, methoxy); 3.13 (2H, doublet, J=6 Hz, hydrogens at 5-position of pyridazine); 2.38 (3H, singlet, CH$_3$).

The following compounds were also prepared by the same procedure:
6-(3-bromophenyl)-4-methoxy-4,5-dihydro-2H-pyridazin-3-one (Compound No. 17), melting at 123°–125° C.;
6-(3,5-dichloro-4-methylphenyl)-4-methoxy-4,5-dihydro-2H-pyridazin-3-one (Compound No. 20), melting at 175°–178° C.; and
6-(3,4-dichlorophenyl)-4-methoxy-4,5-dihydro-2H-pyridazin-3-one (Compound No. 19), melting at 158°–161° C.

EXAMPLE 3

6-(3-Bromophenyl)-4-hydroxy-4,5-dihydro-2H-pyridazin-3-one (Compound No. 10)

0.25 g of hydrazine hydrate was added, at room temperature, to a mixture of 10 ml of ethanol and 1.36 g of 4-(3-bromophenyl)-2-hydroxy-4-oxobutyric acid (prepared following the procedure described in Preparation 3), and then the mixture was heated at 65° C. for 1.5 hours. The crystals which precipitated were collected by filtration at the same temperature and then washed with ethanol, giving 0.78 g (yield 58%) of the pure title compound melting at 158°–161° C.

Infrared Absorption Spectrum (Nujol mull) $\nu_{max}$ cm$^{-1}$: 3500, 3200, 3100, 2800–2100, 1700.

Nuclear Magnetic Resonance Spectrum (heptadeuterated dimethylformamide) δ ppm: 10.95 (1H, singlet, NH); 7.3–8.1 (4H, multiplet, aromatic hydrogens); 6.77 (1H, broad singlet, OH); 4.42 (1H, doublet of doublets, J=6 and 10 Hz, hydrogen at 4-position of pyridazine); 2.7–3.7 (2H, multiplet, hydrogens at 5-position of pyridazine).

The same procedure was followed, to prepare the following compounds:
6-(3,5-dichloro-4-methylphenyl)-4-hydroxy-4,5-dihydro-2H-pyridazin-3-one (Compound No. 16), melting at 213°–215° C.;
6-(3,4-dichlorophenyl)-4-hydroxy-4,5-dihydro-2H-pyridazin-3-one (Compound No. 15), melting at 196°–200° C.;
4-hydroxy-6-(4-methylphenyl)-4,5-dihydro-2H-pyridazin-3-one (Compound No. 13), melting at 174°–178° C.;
6-(4-chlorophenyl)-4-hydroxy-4,5-dihydro-2H-pyridazin-3-one (Compound No. 11), melting at 186°–189° C.;
6-(4-fluorophenyl)-4-hydroxy-4,5-dihydro-2H-pyridazin-3-one (Compound No. 12), melting at 197°–199° C.; and
4-hydroxy-6-(4-methoxyphenyl)-4,5-dihydro-2H-pyridazin-3-one (Compound No. 14), melting at 179°–183° C.

PREPARATION 1

4-(3,5-Dichloro-4-methylphenyl)-3-hydroxy-4-oxobutyric acid 2.96 g of 3-chloro-4-(3,5-dichloro-4-methylphenyl)-4-oxobutyric acid were added to 300 ml of a 10% w/v aqueous solution of sodium carbonate, and then the resulting mixture was stirred at room temperature for 3 hours. The reaction mixture was periodically checked by thin layer chromatography and, when the spot due to the starting material had disappeared, the mixture was poured into a mixture of 500 g of crushed ice and 50 ml of concentrated hydrochloric acid. It was then extracted with diethyl ether. The ethereal extract was dried over anhydrous sodium sulfate and the solvent was then distilled off. There were obtained 2.65 g (yield 96%) of the title compound in an impure form. To this material was added a small amount of benzene, and then hexane, yielding 1.28 g (yield 46%) of the title compound in the form of pure crystals, melting at 114.5°–117.5° C.

Following the same procedure, but employing different substituted oxobutyric acids, the following compounds were also prepared:

4-(3-bromophenyl)-3-hydroxy-4-oxobutyric acid, melting at 129°–130° C.;

4-(3,4-dichlorophenyl)-3-hydroxy-4-oxobutyric acid, melting at 135°–138° C.;

4-(3,5-dichloro-4-methoxyphenyl)-3-hydroxy-4-oxobutyric acid, melting at 123°–126° C.; and 3-hydroxy-4-(4-methylphenyl)-4-oxobutyric acid, melting at 113°–114° C.

PREPARATION 2

4-(3-Bromophenyl)-2-methoxy-4-oxobutyric acid

A mixture of 4 g of 4-(3-bromophenyl)-4-oxo-2-butenoic acid, 2.2 g of anhydrous potassium carbonate and 200 ml of methanol was stirred at room temperature for 8 hours; 5 ml of concentrated hydrochloric acid were then added, with ice-cooling, to acidify the resulting solution. The mixture was then extracted with ethyl acetate, and the extract was washed with water and dried over anhydrous sodium sulfate. The solvent was then distilled from the extract, leaving 4.7 g of a crude material. Trituration of the crude material with diisopropyl ether gave 2 g (yield 44%) of the title compound in a pure form melting at 82.5°–83.5° C.

The following compounds were prepared by the same procedure:

4-(3,5-dichloro-4-methylphenyl)-2-methoxy-4-oxobutyric acid, melting at 118°–120° C.;

4-(3,4-dichlorophenyl)-2-methoxy-4-oxobutyric acid, melting at 99°–101° C.; and 2-methoxy-4-(4-methylphenyl)-4-oxobutyric acid, melting at 92°–95° C.

PREPARATION 3

2-Hydroxy-4-(4-methylphenyl)-4-oxobutyric acid

A mixture of 6.7 g of 4-methylacetophenone, 12.42 g of glyoxylic acid monohydrate, 12.6 g of sodium bicarbonate, 75 ml of methanol and 75 ml of water was stirred at a temperature of 50°–60° C. for 12 hours. At the end of this time, the pH was adjusted to a value of 4 by the addition of dilute hydrochloric acid, and then the reaction mixture was extracted with ethyl acetate. The extract was dried over anhydrous sodium sulfate and then the solvent was evaporated off under reduced pressure, leaving 9.98 g of a residue. This residue was subjected to column chromatography through silica gel eluted with mixtures of benzene and ethyl acetate ranging from 10:1 to 1:1 by volume. There were obtained 6.8 g (yield 65%) of the title compound, melting at 92°–100° C.

The following compounds were prepared by the same procedure:

4-(3-bromophenyl)-2-hydroxy-4-oxobutyric acid, melting at 108°–110° C.;

4-(3,5-dichloro-4-methylphenyl)-2-hydroxy-4-oxobutyric acid, melting at 141°–143° C.;

4-(3,4-dichlorophenyl)-2-hydroxy-4-oxobutyric acid, melting at 146°–151° C.;

4-(4-chlorophenyl)-2-hydroxy-4-oxobutyric acid, melting at 138°–140° C.;

4-(4-fluorophenyl)-2-hydroxy-4-oxobutyric acid, melting at 128°–130° C.; and 2-hydroxy-4-(4-methoxyphenyl)-4-oxobutyric acid, melting at 122°–126° C.

EXAMPLE 4

Dust 5 parts of Compound No. 1, 50 parts of talc and 45 parts of kaolin were uniformly mixed to form a dust.

EXAMPLE 5

Wettable powder 50 parts of Compound No. 2, 29 parts of clay, 10 parts of diatomaceous earth, 5 parts of white carbon, 3 parts of sodium ligninsulfonate, 2 parts of Newcol 1106 (a trade name of Nihon Nyukazai K.K., Japan) and 1 part of polyvinyl alcohol were uniformly mixed in a mixer and then pulverized three times by a hammer mill, to give a wettable powder.

EXAMPLE 6

Granules 70 parts of Compound No. 1 were finely pulverized, and then 30 parts of clay were added and the whole was mixed in a mixer to form a premix. 10 parts of this premix were uniformly mixed with 60 parts of clay and 30 parts of bentonite in a mixer. The mixture was then kneaded with a suitable amount of water in a kneader, extruded through a screen having apertures of diameter 0.8 mm and then dried in a draught drier at 50° C. The resulting product was formed into granules by means of a sifter.

The following Examples 7–9 illustrate the use and activity of the agricultural fungicides of the present invention. In these Examples, the compounds of the invention were employed in the form of a wettable powder, prepared as described in Example 5, and containing 50% by weight of the active compound.

EXAMPLE 7

Preventive effect against sheath blight of rice plants

Rice seedlings of the variety Nihonbare at the 4–5 leaf stage were sprayed with 50 ml of test preparation per 3 pots; each test preparation contained 30 ppm of one of the active compounds of the invention. The treated plants were kept at room temperature for 24 hours, after which they were infected with sheath blight by placing around the lower part of the stem of each seedling 4–5 oat grains on which the pathogenic fungus of rice sheath blight (*Rhizoctonia solani*) had previously been cultured. The plants were then placed in a moist room at 25°–27° C. Seven days after infection, the extent of the disease was investigated by determining the height of the diseased area (in cm).

A similar experiment was carried out as a control, except that the text preparation contained no active compound. The results obtained are shown in Table 1.

TABLE 1

| Compound No. | Height of diseased spot (cm) |
|---|---|
| 1 | 5.2 |
| 5 | 6.5 |
| 7 | 0.5 |
| 9 | 6.3 |
| 17 | 10.1 |
| 20 | 9.8 |
| Untreated control | 17.6 |

EXAMPLE 8

Preventive effect against sheath blight of rice plants under simulated paddy field conditions Rice seedlings of the variety Nihonbare at the 4–5 leaf stage grown in pots were flooded to a depth of 1 cm with water and the water level was maintained at this level. A test preparation containing the active compound was applied in an amount corresponding to 800 g of active compound per 10 ares onto the pots, which were then placed in a greenhouse. After keeping the plants in the greenhouse for seven days, the surface water was drained from the pots and the plants were infected with sheath blight by placing 4–5 oat grains on which the pathogenic fungus of rice sheath blight had previously been cultured around the lower part of the stem of each seedling. The treated plants were then placed in a moist room maintained at a temperature of 25°–27° C. and, seven days after infection, the extent of the disease was determined as the height of the diseased area (in cm). A similar experiment was carried out as a control, but no active compound was applied. The results obtained are shown in Table 2.

TABLE 2

| Compound No. | Height of diseased spot (cm) |
|---|---|
| 1 | 0 |
| 5 | 3.4 |
| 7 | 4.1 |
| 9 | 2.4 |
| 10 | 2.5 |
| 17 | 0 |
| 18 | 7.2 |
| Untreated control | 18.1 |

EXAMPLE 9

Fungicidal effect against damping-off on kidney beans by seed dressing

The pathogenic fungus of damping-off of kidney beans (Rhizoctonia solani), which had been cultured on an oat grain medium at 26° C. for 2 weeks, was homogeneously mixed with soil. The soil was then placed into plastic boxes (each of dimensions 25 cm×35 cm, depth 11 cm), and 60 grains of kidney bean seeds of the variety Masterpiece (which had been dressed with a test preparation containing one of the active compounds of the invention in an amount of 0.25% of the seed weight) were sown into this soil. The boxes were then kept in a greenhouse at 25° C. for 2 weeks, after which the number of infected seedlings was determined. A similar experiment was carried out as a control, but in which the seeds were not dressed with a fungicidal dressing. The results are summarized in Table 3.

TABLE 3

| Compound No. | No. of infected seedlings |
|---|---|
| 1 | 3 |
| 5 | 8 |
| 7 | 13 |
| 9 | 7 |
| 10 | 9 |
| 17 | 2 |
| 18 | 18 |
| Untreated control | 60 |

We claim:

1. A method of preventing or controlling fungal attack on plant material by applying to said material or to a locus including the same an effective amount of a fungicide, wherein the fungicide comprises at least one compound of the formula (I):

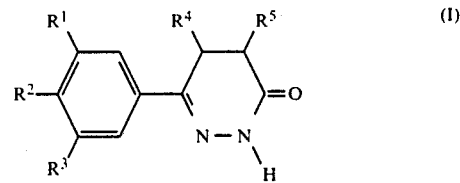

wherein
$R^1$ represents a halogen atom;
$R^2$ represents hydrogen, a $C_1$–$C_3$ alkyl group, a $C_1$–$C_3$ alkoxy group or a halogen atom;
$R^3$ represents a hydrogen or a halogen atom; and at least one of $R^4$ and $R^5$ represents hydrogen and the other represents hydroxy.

2. The method as claimed in claim 1, in which:
$R^1$ represents a halogen atom;
$R^2$ represents hydrogen, a halogen atom or a $C_1$–$C_3$ alkyl group; and
$R^3$ represents a hydrogen or halogen atom.

3. The method as claimed in claim 2, in which:
$R^1$ and $R^3$ both represent halogen atoms (which may be the same or different); and
$R^2$ represents a $C_1$–$C_3$ alkyl group or a halogen atom.

4. The method as claimed in claim 2, in which:
$R^1$ represents a halogen atom;
$R^2$ represents a hydrogen or halogen atom; and
$R^3$ represents hydrogen.

5. The method as claimed in claim 2, in which $R^4$ represents hydroxy and $R^5$ represents hydrogen.

6. The method as claimed in claim 2, in which $R^4$ represents hydrogen and $R^5$ represents hydroxy.

7. The method as claimed in claim 1, wherein said fungicide is selected from the group consisting of:
6-(3-bromophenyl)-5-hydroxy-4,5-dihydro-2H-pyradazin-3-one,
6-(3,4-dichlorophenyl)-5-hydroxy-4,5-dihydro-2H-pyridazin-3-one,
6-(3,5-dichloro-4-methylphenyl)-5-hydroxy-4,5-dihydro-2H-pyradazin-3-one,
6-(3,5-dichloro-4-methoxyphenyl)-5-hydroxy-4,5-dihydro-2H-pyridazin-3-one,
6-(3-bromophenyl)-4-hydroxy-4,5-dihydro-2H-pyridazin-3-one,
6-(3,4-dichlorophenyl)-4-hydroxy-4,5-dihydro-2H-pyridazin-3-one, and 6-(3,5-dichloro-4-methylphenyl)-4-hydroxy-4,5-dihydro-2H-pyridazin-3-one.

8. The method as claimed in claim 1, wherein said plant material is a growing plant.

9. The method as claimed in claim 8, wherein said fungicide is applied by spraying said growing plant.

10. The method as claimed in claim 8 or claim 9, wherein said fungicide is selected from the group consisting of:

6-(3-bromophenyl)-5-hydroxy-4,5-dihydro-2H-pyridazin-3-one, 6-(3,4-dichlorophenyl)-5-hydroxy-4,5-dihydro-2H-pyridazin-3-one, 6-(3,5-dichloro-4-methylphenyl)-5-hydroxy-4,5-dihydro-2H-pyridazin-3-one, 6-(3,5-dichloro-4-methoxyphenyl)-5-hydroxy-4,5-dihydro-2H-pyridazin-3-one, 6-(3-bromophenyl)-4-hydroxy-4,5-dihydro-2H-pyridazin-3-one, 6-(3,4-dichlorophenyl)-4-hydroxy-4,5-dihydro-2H-pyridazin-3-one, and 6-(3,5-dichloro-4-methylphenyl)-4-hydroxy-4,5-dihydro-2H-pyridazin-3-one.

11. The method as claimed in claim 1, wherein
$R^1$ represents bromide or chlorine,
$R^2$ represents hydrogen, chlorine, methyl or methoxy, and
$R^3$ represents hydrogen or chlorine.

12. The method as claimed in claim 8, wherein
$R^1$ represents bromide or chlorine,
$R^2$ represents hydrogen, chlorine, methyl or methoxy, and
$R^3$ represents hydrogen or chlorine.

13. The method as claimed in claim 1 or claim 9, wherein said fungicide is 6-(3-bromophenyl)-5-hydroxy-4,5-dihydro-2H-pyridazin-3-one.

14. The method as claimed in claim 1 or claim 9, wherein said fungicide is 6-(3,4-dichlorophenyl)-5-hydroxy-4,5-dihydro-2H-pyridazin-3-one.

15. The method as claimed in claim 1 or claim 9, wherein said fungicide is 6-(3,5-dichloro-4-methylphenyl)-5-hydroxy-4,5-dihydro-2H-pyridazin-3-one.

16. The method as claimed in claim 1 or claim 9, wherein said fungicide is 6-(3,5-dichloro-4-methoxyphenyl)-5-hydroxy-4,5-dihydro-2H-pyridazin-3-one.

17. The method as claimed in claim 1 or claim 9, wherein said fungicide is 6-(3-bromophenyl)-4-hydroxy-4,5-dihydro-2H-pyridazin-3-one.

18. The method as claimed in claim 1 or claim 9, wherein said fungicide is 6-(3,4-dichlorophenyl)-4-hydroxy-4,5-dihydro-2H-pyridazin-3-one.

19. The method as claimed in claim 1 or claim 9, wherein said fungicide is 6-(3,5-dichloro-4-methylphenyl)-4-hydroxy-4,5-dihydro-2H-pyridazin-3-one.

* * * * *